United States Patent [19]

Karapetian

[11] Patent Number: 5,344,762

[45] Date of Patent: Sep. 6, 1994

[54] METHOD FOR THE EARLY DIAGNOSIS OF CANCER

[75] Inventor: Anait Karapetian, Tel Aviv, Israel

[73] Assignee: ERA-Masis, Ltd., Tel Aviv, Israel

[21] Appl. No.: 38,674

[22] Filed: Mar. 26, 1993

[30] Foreign Application Priority Data

Mar. 29, 1992 [IL] Israel .................................. 101.409

[51] Int. Cl.$^5$ .................. C12Q 1/06; G01N 33/48
[52] U.S. Cl. ........................................ 435/39; 435/4; 435/36; 435/38; 435/848; 435/885; 436/63; 436/64
[58] Field of Search ............... 435/39, 4, 36, 38, 848, 435/885; 436/63, 64

[56] References Cited

U.S. PATENT DOCUMENTS 4,582,787  4/1986  Frankel ................................. 435/5

FOREIGN PATENT DOCUMENTS 54-143528  4/1978  Japan .

OTHER PUBLICATIONS

Acevedo et al, *Journal of General Microbiology*, vol. 133, pp. 783–791, 1987.

Garbitelli et al, *JAMA*, vol. 247, No. 13, p. 1812, Apr. 2, 1982.

Oleynik, S. F. and Panchishina, M. V., "About Coli-flora and Cancerolycity and Carcinogenicity of the Intestine", Vrachebnoye-delo, 1968, 5:13–17.

*Primary Examiner*—Michael G. Wityshyn
*Assistant Examiner*—Abdel A. Mohamed
*Attorney, Agent, or Firm*—Brumbaugh, Graves, Donohue & Raymond

[57] ABSTRACT

In a method for early diagnosis of human cancer, a human fecal sample of bacteria (*Escherichia coli* and/or *Streptococcus faecalis*), is incubated in vitro with a standard culture of a known number of cancer cells, for a period of time sufficient to enable the extent of interaction between the bacteria and the standard culture of cancer cells to be determined; the number of the interacted and/or non-interacted cancer cells present at the end of the period is determined and is utilized for the diagnosis based on the calculation of a tumor cell necrosis index (TCNI). The extent of interaction referred to may be calibrated against analogous interaction using a control preparation of bacteria, e.g. *Escherichia coli* A.T.C.C. 55373, 55374 and/or 55375, and/or *Streptococcus faecalis* A.T.C.C. 55376.

12 Claims, No Drawings

METHOD FOR THE EARLY DIAGNOSIS OF CANCER

FIELD AND BACKGROUND OF THE INVENTION

The present invention relates to a method for the early diagnosis of cancer. In spite of the vast research and clinical effort which has been made in the past, in relation to investigation of the occurrence, diagnosis and treatment of cancer, many problems of an etiological and pathogenetic nature, and which bear on the identification, prevention and treatment of cancer, must be regarded as still in need of a solution.

However, it is generally agreed that early diagnosis of the disease is almost always a prerequisite of successful treatment. For example, the WHO Expert Committee's Report on Early Detection of Cancer (1969) stated that over half of cancer patients could have been cured if the disease had been detected at an early stage and treated soon after detection. In view of the widespread incidence of the disease, mass screening techniques would evidently be of great value, but have not been instituted on a worldwide basis up to the present time, such as is available for example, at least in developed countries, in the field of tuberculosis of the chest by means of mass X-ray examination.

Among previous proposals for the diagnosis of cancer may be mentioned the following. In U.S. Pat. No. 3,476,514, there was described a method of detecting cancer cells by staining test cells with acriflavine-HCl solution, determining indirectly the dye absorbed by the test cells and comparing with a control. JP 54143528 proposed a method for diagnosing malignant tumors which utilized an injectable composition containing an endotoxin extracted from cultured bacteria. In GB 1587244, there was described inter alia, the use in a serum agglutination test on the sera of patients, for the detection of neoplasms, of an antigen produced by a species of the genus Streptococcus.

Bodily health is known to be affected by the nature of the intestinal flora, which apparently influences, for example, metabolic processes and both local and general body immune response. It has also been known for some time that certain of the intestinal flora bacteria of normal humans have oncolytic activity, and that there exists a relationship between intestinal microfloral composition and cancer morbidity, see e.g., Oleynik, S.F. and Panchishina, M.V., "About Coliflora and Cancerolycity and Carcinogenicity of the Intestine", Vrachebnoye-delo, 1968, 5:13-17. However, mere knowledge of a relationship between the intestinal microflora, the immune system and cancer has not resulted up to now in the development of a reliable method for the early diagnosis of cancer.

SUMMARY OF THE INVENTION

The present invention provides a method for the early diagnosis of cancer in a human, wherein a human feces-derived sample of bacteria selected from *Escherichia coli* and *Streptococcus faecalis*, is subjected to incubation in vitro with a standard culture of cancer cells containing a predetermined number of such cells, for a period of time sufficient to enable the extent of interaction between the bacteria and the standard culture of cancer cells to be determined, and effecting the determination based on a count of the number of the interacted and/or non-interacted cancer cells present at the end of the period of time.

The expression "early diagnosis of cancer" in the present specification and claims, is intended to convey such diagnosis, whether or not the cancer has reached the stage in which it is detectable by other methods presently available to the clinician.

DETAILED DESCRIPTION OF THE INVENTION

In a particular embodiment by which the present invention may be practiced, determination of the extent of interaction between the test sample of bacteria and the standard culture of cancer cells is made by counting the number of cancer cells remaining in the visual field of a microscope of a smear on a microscope slide, after fixing and dyeing as necessary. The operative methods for counting cells on a microscope slide are per se known to persons in the field.

In order to avoid errors and for the sake of improved accuracy in the determination, it is preferred that determination of the extent of interaction between the bacteria and the standard culture of cancer cells be calibrated against the extent of interaction between a control preparation of bacteria incubated under the same conditions, and the standard culture of cancer cells.

Thus, for example, when carrying out a control determination in addition to the test determination, there may be calculated a Tumor Cell Necrosis Index (TCNI) from the following formula $c(\%) = 100(a-b)/a$, where $a$ = the number of standard cancer cells destroyed in the control experiment, $b$ = the number of standard cancer cells not destroyed in the experiment on the test sample, and $c$ = the TCNI. Qualitatively, it will be apparent that in a healthy patient in which the intestinal *Escherichia coli* and *Streptococcus faecalis* will have a similar activity to the control bacteria, $b$ will be low (and $a$ in any case should be approaching 100%), giving a relatively high TCNI, whereas in a relatively less healthy patient $b$ will have a relatively high value and the TCNI will be lower. More precisely, the inventors have found the TCNI values indicated in Table 1 in relation to healthy patients and patients having various classes of diseases.

TABLE 1

| Diseases | No. of patients | c(average) | Sigma | c(range) |
|---|---|---|---|---|
| (Normal subjects) | 1200 | 86 | 1.1 | 68–100 |
| Gastrointestinal | 1340 | 62 | 1.1 | 50–98 |
| Tuberculosis | 141 | 70 | 2.3 | 67–100 |
| Communicable | 123 | 62 | 1.1 | 60–89 |
| Radiation | 157 | 52 | 1.1 | 30–56 |
| Oncological | 1531 | 29 | 1.1 | 10–49 |
| Oncological post-operative | 682 | 53 | 3.4 | 21–82 |

It should be particularly noted that the c range of 68–100 for normal human subjects does not overlap the c range of 10–49 found for oncological subjects. These facts underline the precision and thus the utility of the present method for early diagnosis of cancer. Based on their overall experience to date, the inventors believe that c values within these ranges indicate the following in human subjects under test: 49% and below: malignant tumors present in the body; >49% and <61%: the subjects have a possible predisposition to malignant tumors, i.e. a potential risk group; 61–100%: absence of malignant tumors in the body.

Without prejudice to the broad concept of the invention as set forth herein, suitable strains of bacteria for use as control, in a preferred embodiment of the method of the invention, are the following four strains, isolated from healthy human feces, which have been deposited with the American Type Culture Collection (A.T.C.C.) of address 12301 Parklawn Drive, Rockville, Md. 20852, under the Budapest Treaty, on Nov. 13 1992.

*Escherichia coli* G35 strain no. 1-59, A.T.C.C. Designation 55373.

Cultural and morphological features indicate that the strain belongs to the Escherichia genus. The straight rods of 1.1–1.5×2.0–6.0 mm (alive) occur separately or in pairs, and are gram-negative. They are mobile, and move using peritracheal cilia. They form pink-colored colonies in endomedium; nutritional agar colonies are smooth, moist, greyish with regular edges; gelatin colonies are turbid, greyish-white, moist. When grown on potato they give an extensive yellowish diffused coating. The strain is preserved in 2% plain agar, in a refrigerator at 4°–8° C., with weekly reincubation. Reproduction is by incubation at 37° C. (thermostat) for 24 hours. Oncolytic activity is shown under incubation at 37° C. (thermostat) for 2–6 hours in contact with tumor cells, in vitro, as well as under in vivo conditions by administration per os.

The culture generates indole but not hydrogen sulfide, gives negative Voges-Proskauer reaction and positive reaction with methyl red. It does not eliminate urea and does not utilize citrate. It does not ferment rhamnose, raffinose, and salicin. Glucose and other carbohydrates are fermented producing pyruvate, which is then converted to lactic, acetic and formic acids. Part of the formic acid is broken down by the complex hydrogen lyase enzymatic system into equal quantities of carbon dioxide and hydrogen. The culture has weak hemolytic properties. The strain is resistant to kanamycin, oxacillin, erythromycin, methicillin, polymyxin, ampicillin, penicillin, oleandomycin, neomycin, streptomycin, rheotomycin and tetracycline, and has low sensitivity to carbenicillin, gentamycin and levomycetin.

*Escherichia coli* G35 strain no. 2-60, A.T.C.C. Designation 55374.

Cultural and morphological features indicate that the strain belongs to the Escherichia genus. The straight rods of 1.1×1.5×2.0–6.0 mm (alive) occur separately or in pairs, and are gram-negative. They are mobile, and move using peritracheal cilia. They form pink-colored colonies in endomedium; nutritional agar colonies are smooth, moist, greyish with regular edges; gelatin colonies are turbid, greyish-white, moist. When grown on potato they give an extensive yellowish diffused coating. The strain is preserved in 2% plain agar, in a refrigerator at 4°–8° C., with weekly reincubation. Reproduction is by incubation at 37° C. (thermostat) for 24 hours. Oncolytic activity is shown under incubation at 37° C. (thermostat) for 2–6 hours in contact with tumor cells, in vitro, as well as under in vivo conditions by administration per os.

The culture generates indole but not hydrogen sulfide, gives negative Voges-Proskauer reaction and positive reaction with methyl red. It does not eliminate urea and does not utilize citrate. It does not ferment dulcite, salicin or cellobiose, but weakly ferments lactose and saccharose (by 6–10 days). Glucose and other carbohydrates are fermented producing pyruvate, which is then converted to lactic, acetic and formic acids. Part of the formic acid is broken down by the complex hydrogen lyase enzymatic system into equal quantities of carbon dioxide and hydrogen. The culture has weak hemolytic properties.

The strain is resistant to kanamycin, oxacillin, erythromycin, methicillin, polymyxin, ampicillin, penicillin, oleandomycin, neomycin, streptomycin, rheotomycin and tetracycline, and has low sensitivity to carbenicillin, gentamycin and levomycetin.

*Escherichia coli* G35 strain no. 3-61, A.T.C.C. Designation 55375.

Cultural and morphological features indicate that the strain belongs to the Escherichia genus. The straight rods of 1.1–1.5×2.0–6.0 mm (alive) occur separately or in pairs, and are gram-negative. They are mobile, and move using peritracheal cilia. They form pink-colored colonies in endomedium; nutritional agar colonies are smooth, moist, greyish with regular edges; gelatin colonies are turbid, greyish-white, moist. When grown on potato they give an extensive yellowish diffused coating. The strain is preserved in 2% plain agar, in a refrigerator at 4°–8° C., with weekly reincubation. Reproduction is by incubation at 37° C. (thermostat) for 24 hours. Oncolytic activity is shown under incubation at 37° C. (thermostat) for 2–6 hours in contact with tumor cells, in vitro, as well as under in vivo conditions by administration per os.

The culture generates indole but not hydrogen sulfide, gives negative Voges-Proskauer reaction and positive reaction with methyl red. It does not eliminate urea and does not utilize citrate. It does not ferment rhamnose, raffinose and salicin. Glucose and other carbohydrates are fermented producing pyruvate, which is then converted to lactic, acetic and formic acids. Part of the formic acid is broken down by the complex hydrogen lyase enzymatic system into equal quantities of carbon dioxide and hydrogen. The culture has weak hemolytic properties.

The strain is resistant to kanamycin, oxacillin, erythromycin, methicillin, polymyxin, ampicillin, penicillin, oleandomycin, neomycin, streptomycin, rheotomycin and tetracycline, and has low sensitivity to carbenicillin, gentamycin and levomycetin.

*Streptococcus faecalis* G35 strain no. 4-62, A.T.C.C. Designation 55376.

Cultural and morphological features indicate that the strain belongs to the Streptococcus faecalis genus. The cells are spherical or oval, in pairs or diversified chains, diameter less than 2 mm. They are stable, do not form endospores and are gram-positive. The strain is preserved in 2% plain agar, in a refrigerator at 4°–8° C., with weekly reincubation. Reproduction is by incubation at 37° C. (thermostat) for 24 hours. Oncolytic activity is shown under incubation at 37° C. (thermostat) for 2–6 hours in contact with tumor cells, in vitro, as well as under in vivo conditions by administration per os.

The culture grows in 6.5% NaCl broth at pH 9.6, or in milk with 0.1% methylene blue. For growth in plain media, folic acid is required. It ferments arabinose and sorbite, but does not produce ammonia from arginine. It contains Lancefield O and D group antigens.

The strain is resistant to kanamycin, oxacillin, erythromycin, methicillin, polymyxin, ampicillin, penicillin, oleandomycin, neomycin, streptomycin, rheotomycin and tetracycline, and has low sensitivity to carbenicillin, gentamycin and levomycetin.

The present invention will now be illustrated by the following non-limitative Examples, of which Examples 2–4 are case studies.

EXAMPLE 1

Isolation and Use of Feces-derived Bacteria

A faeces inoculation of 1.0 g/10 ml saline was made in Endo agar, and a portion of this mixture was added to an agar-agar medium to isolate Streptococcus faecalis, which were placed in an incubator for 24 hours at 37° C. The inoculation was then transferred from Endo agar to 2% plain agar to isolate *Escherichia coli*, and from special medium to blood bile salt agar (BBSA) to further isolate *Streptococcus faecalis*; the isolated bacteria were placed in an incubator for 24 hours at 37° C. The cultures were checked by Gram staining, biochemical tests and the requirements of the Bergi specifications (1980).

The isolated bacteria (20 ml containing 2 billion microbes/ml) were smeared with 0.02 g of a suspension of standard human or animal malignant cancer cells (e.g. sarcoma 45), then the mixture was incubated at 37° C. for 2–6 hours (e.g. 6 hours in the case of sarcoma 45), depending on the strain of cancer cells. In the control experiment 0.4 ml saline solution was mixed with 0.02 g cancer cells; smears were prepared, fixed by the Mai-Grunwald technique and dyed by the Romanovsky-Gimza technique. Thereafter, destroyed and non-destroyed cancer cells were counted in 5 or 10 (H.P. or L.P.) visual fields, the average index was taken and the TCNI was calculated, as explained above, from the equation $c(\%) = 100(a-b)/a$.

EXAMPLE 2

Patient K.R.S. was first examined on Dec. 27, 1979 where she complained of irregular menses; initial uterine myoma was diagnosed. The patient was hospitalized, the uterine cavity was curretted and the myomatous node was excised for identification purposes. On histology, endometrial fragments with fibrosis were identified. According to the technique of the invention described herein, the TCNI was found to be 40%. On Jan. 4, 1979, the patient was discharged in satisfactory condition.

The patient subsequently complained (Jun. 19, 1979) of prolonged menstrual hemorrhage and was again hospitalized. Hysterography was performed and polypold-cystic neoplasm was found in the mucosa of the uterine cervix. An operation was carried out on Sep. 13, 1979, and supravaginal amputation of the uterus without adnexal uteri was performed due to the presence of a submucous myomatous node. Histology confirmed uterine myoma. The patient was discharged Sep. 25, 1979 in satisfactory condition. On Mar. 10, 1982, due to the symptoms indicated above, the patient was operated on with high vaginal cervicectomy with dissection of the cervical canal mucosa and resection of ligation granulation polyps. Surgical intervention was complicated by internal hemorrhage which resulted in laparotomy with abdominal cavity drainage.

On Dec. 2, 1983, due to the occurrence of an ovarian tumor with 7.5 month pregnancy dimensions, laparotomy was performed. When the abdominal cavity was opened, a 14×16 cm right ovarian tumor was found, with numerous adhesions to the parietal peritoneum. After adhesion lysis the tumor was removed. A 10×10 cm left ovarian tumor was also found, with adhesions and infiltrative growth into adjacent organs (bladder, sigmoid colon); the left ovarian tumor was deemed inoperable. Histology of the right ovarian tumor and omental biopsies showed granular cell carcinoma with thecomatosis and metastases involving the omentum and enteric peritoneum.

This case study demonstrates the usefulness of the present invention for early diagnosis of malignant tumors.

EXAMPLE 3

A.A.K., 53, was hospitalized May 27, 1988 and discharged Jun. 8, 1988; clinical diagnosis indicated systemic disease of left lung complicated by exudative pleurisy, as well as osteoma of the left frontal bone. From previous hospital history (May 1988), biopsy of the pleural cavity followed by cytology showed metastasis of adenocarcinoma with effect on the mucosa. The patient first felt dyspnea in May 1988. TCNI as set forth herein was found to be 36%. In the period May 17–26, 1988 the patient had been examined with a resulting diagnosis of exudative pleurisy of ambiguous etiology; pleural punctures were performed with the evacuation of about 1.6 l of hemorrhagic fluid and cytology, as stated above.

This case study demonstrates the correlation of a low TCNI, determined in accordance with the present invention, with the existence of malignant tumor in a patient.

EXAMPLE 4

P.C.G., 56, was hospitalized on Apr. 3, 1980, with diagnosis of left crural melanoma. The 2×2 cm tumor was located in the lower posterior portion of the left crus, of soft consistency, mobile on a narrow pedicle, the inguinal lymph nodes not being enlarged. The TCNI as set forth herein was found to be 30%. On Apr. 9, 1988, electro-dissection of the tumor was effected under local anesthesia, with a normal post-operation period; the sutures were removed on the 10th day. The patient was discharged on Apr. 24, 1980, apparently in good condition. Histology showed cancer. There was no TCNI rise (determined in accordance with the present invention) following surgical intervention. On Jul. 20, 1980, TCNI as determined in accordance with the present invention was found to be 36%. On Sep. 2, 1981, the patient was readmitted to hospital and metastases in the inguinal lymph nodes and in the peritoneum were diagnosed.

This case study demonstrates the correlation of a low TCNI, determined in accordance with the present invention, with the existence of malignant tumor in a patient, and further indicated that the persistence of malignant cancer after the patient had been discharged from initial surgery in apparent good condition.

ADVANTAGES OF THE INVENTION

The present invention has been shown not only to correlate with clinical findings of cancer, but has demonstrated the presence of cancer not found by conventional clinical procedures. The method of the invention is simple to operate, accurate, and involves no discomfort of the human subject under examination. The method of the invention is potentially readily adaptable to mass screening techniques, in order to identify persons with cancer as well as risk groups. Persons skilled in the art will be aware that the counting of destroyed and/or non-destroyed bacteria which forms part of the inventive method is capable of computerization. As appears from the above case studies, the method of the invention can be used to confirm the efficiency of clinical treatment of cancer, and for detection of recurrence of malignant disease.

While particular embodiments of the invention have been particularly shown and/or described hereinabove, it will be appreciated that the present invention is not limited thereto, since, as will be readily apparent to skilled persons, many variations and modifications can be made. Accordingly, the essential concept, spirit and scope of the present invention will be better understood in the light of the claims which follow.

I claim:

1. A method for the early diagnosis of cancer in a human, wherein a human feces-derived sample of bacteria selected from the group consisting of *Escherichia coli* and *Streptococcus faecalis*, is subjected to incubation in vitro with a standard culture of cancer cells containing a predetermined number of cancer cells, for a period of time sufficient to enable the extent of interaction between said bacteria and said standard culture of cancer cells to be determined, the number of the interacted and/or non-interacted cancer cells present at the end of the period of time being determined and being utilized for the purpose of said diagnosis based on the calculation of a tumor cell necrosis index (TCNI).

2. A method according to claim 1, wherein said period of time lies within the range of about 2 to about 6 hours.

3. A method according to claim 1, wherein said determination is made by counting the number of cancer cells remaining in the visual field of a microscope of a smear on a microscope slide, after fixing and dyeing.

4. A method according to claim 2, wherein said determination is made by counting the number of cancer cells remaining in the visual field of a microscope of a smear on a microscope slide, after fixing and dyeing.

5. A method for the early diagnosis of cancer in a human, wherein a human feces-derived sample of bacteria selected from the group consisting of *Escherichia coli* and *Streptococcus faecalis*, is subjected to incubation in vitro with a standard culture of cancer cells containing a predetermined number of cancer cells, for a period of time sufficient to enable the extent of interaction between said bacteria and said standard culture of cancer cells to be determined, the number of the interacted and/or non-interacted cancer cells present at the end of the period of time being determined and being utilized for the purpose of said diagnosis based on the calculation of a tumor cell necrosis index (TCNI), and wherein said extent of interaction between said bacteria and said standard culture of cancer cells is calibrated against the extent of interaction between a control preparation of bacteria incubated under the same conditions and said standard culture of cancer cells.

6. A method according to claim 5, wherein said period of time lies within the range of about 2 to about 6 hours.

7. A method according to claim 5, wherein said determination is made by counting the number of cancer cells remaining in the visual field of a microscope of a smear on a microscope slide, after fixing and dyeing.

8. A method according to claim 6, wherein said determination is made by counting the number of cancer cells remaining in the visual field of a microscope of a smear on a microscope slide, after fixing and dyeing.

9. A method for the early diagnosis of cancer in a human, wherein a human feces-derived sample of bacteria selected from the group consisting of *Escherichia coli* and *Streiptococcus faecalis*, is subjected to incubation in vitro with a standard culture of cancer cells containing a predetermined number of cancer cells, for a period of time sufficient to enable the extent of interaction between said bacteria and said standard culture of cancer cells to be determined, the number of the interacted and/or non-interacted cancer cells present at the end of the period of time being determined and being utilized for the purpose of said diagnosis based on the calculation of a tumor cell necrosis index (TCNI), wherein said extent of interaction between said bacteria and said standard culture of cancer cells is calibrated against the extent of interaction between a control preparation of bacteria incubated under the same conditions and said standard culture of cancer cells, and wherein in said control preparation of bacteria, there is used at least one strain selected from the group consisting of *Escherichi coli* A.T.C.C. 55373, *Escherichia coli* A.T.C.C. 55374, *Escherichia coli* A.T.C.C. 55375 and *Streptococcus faecalis* A.T.C.C. 55376.

10. A method according to claim 9, wherein said period of time lies within the range of about 2 to about 6 hours.

11. A method according to claim 9, wherein said determination is made by counting the number of cancer cells remaining in the visual field of a microscope of a smear on a microscope slide, after fixing and dyeing.

12. A method according to claim 10, wherein said determination is made by counting the number of cancer cells remaining in the visual field of a microscope of a smear on a microscope slide, after fixing and dyeing.

* * * * *